United States Patent [19]

Wolff et al.

[11] Patent Number: 4,812,576
[45] Date of Patent: Mar. 14, 1989

[54] IMINO DERIVATIVES OF 4-HALOGEN-PYRAZOLONE-5

[75] Inventors: Erich Wolff, Solingen; Dieter Lowski, Bergheim; Harry Elias, Leverkusen, all of Fed. Rep. of Germany

[73] Assignee: Agfa-Gevaert Aktiengesellschaft, Leverkusen, Fed. Rep. of Germany

[21] Appl. No.: 26,160

[22] Filed: Mar. 16, 1987

[30] Foreign Application Priority Data

Mar. 29, 1986 [DE] Fed. Rep. of Germany ....... 3610702

[51] Int. Cl.$^4$ ............................................. C07D 231/38
[52] U.S. Cl. ..................................... 548/362; 548/262
[58] Field of Search ............................................. 548/362

[56] References Cited

U.S. PATENT DOCUMENTS 3,646,059  2/1972  Brantley ............................... 548/362
4,316,039  2/1982  Plath et al. ........................... 548/362

FOREIGN PATENT DOCUMENTS 10068  1/1987  Japan ................................... 548/362

Primary Examiner—Robert W. Ramsuer
Attorney, Agent, or Firm—Connolly & Hutz

[57] ABSTRACT

Imino derivatives of 4-halogen-pyrazolone-5 (formula I) are valuable intermediate products for the preparation of 7-halogen-pyrazolo[3,2-c]-s-triazole magenta couplers.

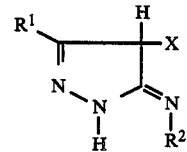

In formula I,
 X denotes chlorine or bromine,
 $R^1$ denotes H, alkyl with 1 to 18 carbon atoms, preferably 1 to 4 carbon atoms, or a substituted or unsubstituted phenyl group;
 $R^2$ denotes H, $NH_2$ or $NJ$-$CO$-$R^3$, and
 $R^3$ denotes alkyl with 1 to 18 carbon atoms, aralkyl, aryl, a heterocyclic group or COOH.

2 Claims, No Drawings

IMINO DERIVATIVES OF 4-HALOGEN-PYRAZOLONE-5

This invention relates to new compounds corresponding to formula I (imino derivatives of 4-halogen-pyrazolone-5), to a process for their preparation and to their use for the preparation of known pyrazolo[3,2-c]-s-triazole compounds substituted in the 7-position which may be used as 2-equivalent magenta couplers in colour photographic recording materials.

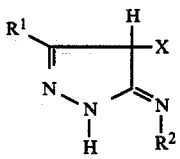

In Formula I,
X denotes chlorine or bromine,
$R^1$ denotes H, alkyl with 1 to 18 carbon atoms, preferably 1 to 4 carbon atoms, or a substituted or unsubstituted phenyl group,
$R^2$ denotes H, $NH_2$ or $NH-CO-R^3$, and
$R^3$ denotes alkyl with 1 to 18 carbon atoms, aralkyl, aryl, a heterocyclic group or COOH.

It is known to use 2-equivalent magenta couplers derived from pyrazolo[3,2-c]-s-triazole in colour photographic recording materials. These magenta couplers have considerable advantages over the hitherto frequently used 2-equivalent magenta couplers derived from pyrazolone-5 in particular in their colour reproduction (J. Chem. Soc. Perkin I, 1977, 2047).

The preparation of pyrazolo[3,2-c]-s-triazole-2-equivalent magenta couplers is, however, complicated and entails considerable difficulties partly due to the complicated nature of the method of synthesizing the bicyclic ring system, including reactions which are difficult to control on a technical scale and provide only low yields. The introduction of halogen atoms which are required for the formation of 2-equivalent couplers and are subsequently split off in the process of colour development is also complicated since it requires saponification and decarboxylation followed by halogenation. The decarboxylation reaction is also difficult to control on a technical scale and halogenation frequently gives rise to dihalogenated products from which one halogen atom must subsequently be removed, e.g. by means of ascorbic acid or triethylphosphite (Synthesis 1985, No. 3, pages 299-300).

The following path of synthesis is known for building up the pyrazolo[3,2-c]-s-triazole ring system:
1.
(a)

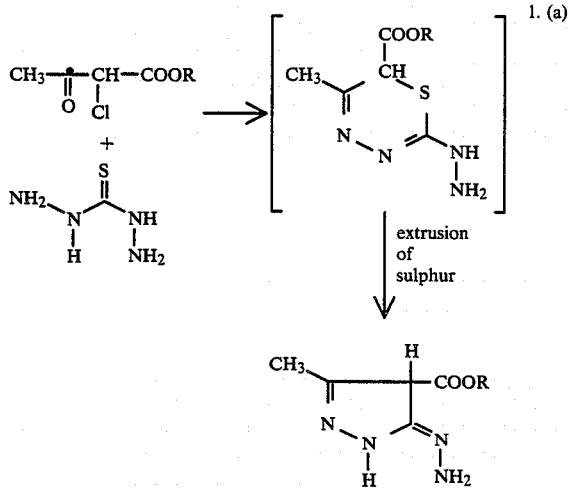

Poor yield:
About 23% of theoretical, J. Chem. Soc. Perkin I, 1977, 2049 about 30% of theoretical, Chem. Ber. 89, 2552 (1956).
  (b) Acylation and ring closure
    DE-A-1 810 462
    DE-A-1 810 463
    DE-A-1 810 464
  (c) Saponification and decarboxylation
    DE-A-1 810 462
    poor yield.
2. Research Disclosure 12 443 (August 1974)

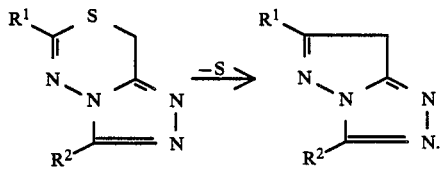

The thermal extrusion of sulphur is possible only with certain substituents $R^1$ and $R^2$ and gives moderate to poor yields.
2. Arch. Pharm. 303, 709 (1970)
    J. Heterocyclic Chem., 11, 751 (1974)

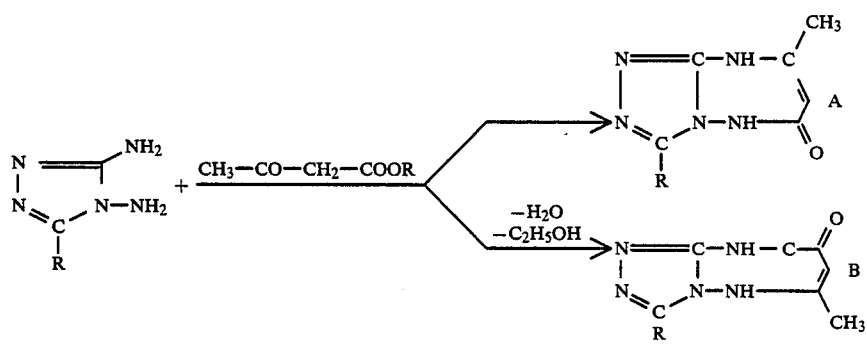

Only compound B of the isomeric mixture was converted into the desired pyrazolotriazole by treatment with acetic anhydride at 140° C., and then only in poor yields. Moreover, the 4,5-diamino-s-triazoles required as starting materials can only be obtained by processes requiring several stages.

4. J. G. O. Becker, H. Böttcher: J. Prakt. Chem. 314, 55 (1972)

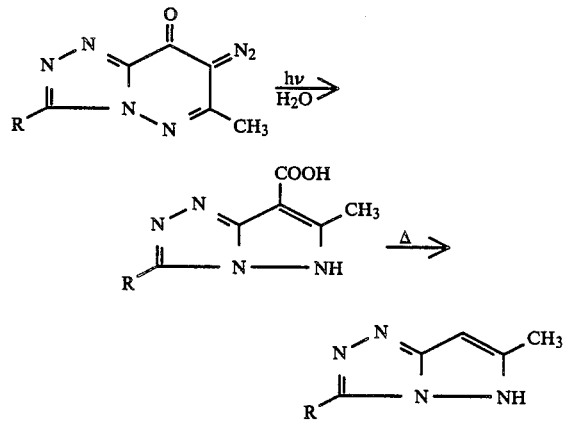

This has the disadvantage that photolysis of the diazoketone followed by thermal decarboxylation is difficult to achieve on a technical scale.

It is an object of the present invention to provide a new, advantageous overall process for the preparation of compounds corresponding to the following formula II which may be used as 2-equivalent magenta couplers.

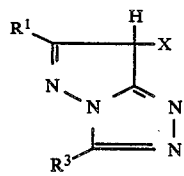

In formula II,
X denotes chlorine or bromine,
$R^1$ denotes H, alkyl with 1 to 18 carbon atoms or a substituted or unsubstituted phenyl group,
$R^3$ denotes alkyl with 1 to 18 carbon atoms, aralkyl, aryl, a heterocyclic aromatic group or COOH.

New compounds corresponding to formula I have now been found which can be converted into the known compounds of formula II by a sequence of easily controlled reactions. Formula I represents only one of several conceivable tautomeric forms of the given compounds but it goes without saying that this formula I is used to represent the compounds as such and therefore all the tautomeric forms. In addition, the formula I covers the salts of the compounds according to the invention, e.g. their hydrohalides.

In formula I, an alkyl group denoted by $R^1$ may be, for example, methyl, ethyl, propyl, isopropyl, butyl, t-butyl, $C_5H_{11}$, $C_6H_{13}$, $C_{13}H_{27}$ or $C_{17}H_{35}$. Such alkyl groups may be substituted, for example with alkoxy. A phenyl group denoted by $R^1$ may be substituted, for example, with alkyl or alkoxy.

The compounds of formula I are imino derivatives of 1H-4-halogen-pyrazolone-5, in particular
imines ($R^2=H$),
hydrazones ($R^2=NH_2$) or
acylhydrazones ($R^2=NH-CO-R^3$).

An alkyl group denoted by $R^3$ may be, for example, methyl, ethyl, propyl, isopropyl, butyl, isobutyl, t-butyl, $C_5H_{11}$, $C_6H_{13}$, 2,4,4-trimethylpentyl, undecyl, $C_{13}H_{27}$, $C_{15}H_{31}$ or $C_{17}H_{35}$. Such alkyl groups may substituted, for example, with alkoxy, aroxy, alkyl sulfonyl or arylsulfonyl.

When $R^3$ denotes an aralkyl group this may be, for example, a benzyl, phenethyl or ω-phenylpropyl group and the phenyl group contained in the aralkyl group may in turn be substituted, e.g. by halogen, alkoxy, nitro or acylamino.

When $R^3$ denotes an aryl group or a substituent containing an aryl group, such aryl group may be in particular a phenyl group which may be substituted, e.g. by alkyl, alkoxy, chlorine or amino groups.

An example of a heterocyclic group denoted by $R^3$ is thienyl.

Examples of compounds according to the invention corresponding to formula I are given below.

TABLE 1

| Compd. | $R^1$ | $R^2$ | $R^3$ | X |
|---|---|---|---|---|
| 1 | CH₃–C(CH₃)(CH₃)– | —NH₂ | — | Cl |
| 2 | $C_2H_5$— | —NH₂ | — | Cl |
| 3 | $CH_3$— | —NH—CO—$R^3$ | —(CH₂)₂—C₆H₄—NO₂ | Cl |
| 4 | $C_{16}H_{33}O$—C₆H₄— | —NH₂ | — | Cl |

TABLE 1-continued

| Compd. | R¹ | R² | R³ | X |
|---|---|---|---|---|
| 5 | $O_2N$-C$_6$H$_4$-(CH$_2$)$_3$- | -NH-CO-R³ | n-C$_4$H$_9$ | Cl |
| 6 | (CH$_3$)$_2$CH- | -NH$_2$ | — | -Br |
| 7 | C$_{12}$H$_{25}$- | -NH-CO-R³ | n-C$_6$H$_{13}$- | -Cl |
| 8 | CH$_3$- | -NH-CO-R³ | -(CH$_2$)$_3$-C$_6$H$_4$-NO$_2$ | -Cl |
| 9 | (CH$_3$)$_3$C- | -NH-CO-R³ | -CH$_2$-CH$_2$-SO$_2$-C$_{18}$H$_{37}$ | Cl |
| 10 | (CH$_3$)$_3$C- | -NH-CO-R³ | -CH(CH$_3$)-CH$_2$-SO$_2$-C$_6$H$_3$(OC$_4$H$_9$)(C$_8$H$_{17}$) | Cl |
| 11 | CH$_3$- | -NH-CO-R$_3$ | -C(CH$_3$)$_2$-CH$_2$-SO$_2$-C$_{18}$H$_{37}$ | Cl |
| 12 | (CH$_3$)$_2$CH- | -NH-CO-R³ | -CH(CH$_3$)-CH$_2$-SO$_2$-C$_6$H$_4$-OC$_{12}$H$_{25}$ | Cl |
| 13 | CH$_3$- | -NH-CO-R³ | -C(C$_4$H$_9$)(C$_2$H$_5$)-SO$_2$-C$_{12}$H$_{25}$ | Cl |

Compounds of formula I in which R²=H can easily be prepared in high yields with a high degree of purity. It has been found that the corresponding compounds of formula I in which X is chlorine may be obtained by reacting the corresponding 5-pyrazoloneimines which are unsubstituted in the 4-position with sulphuryl chloride in warm water.

The present invention therefore also relates to a single stage or multistage process for the preparation of compounds corresponding to formula I in which X stands for chlorine, including a (first) process stage A which is characterised in that 5-pyrazoloneimines corresponding to formula III

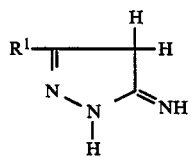
III wherein R¹ has the meaning already indicated are reacted with sulphuryl chloride in aqueous solution or suspension at elevated temperatures, preferably at 50° to 90° C., most preferably at 60° to 80° C. and especially at 65° to 70° C.

The reaction is generally carried out by introducing sulphuryl chloride dropwise into the warm solution or suspension. Since HCl is released in the reaction, it is frequently advantageous to add the hydrochloric acid to the aqueous reaction medium at the very beginning. Furthermore, if the compounds are less readily water-soluble owing to the large size of the group $R^1$, the reaction is advantageously carried out in, for example, an aqueous methanolic solution. The reaction product is generally obtained in crystalline form as the hydrochloride on cooling and may be used in this form for subsequent reactions in the overall process of the invention.

The course of this chlorination reaction is surprising. Conventional methods of chlorination such as chlorination with sulphuryl chloride in organic solvents such as methylene chloride result in the formation of multiply chlorinated products which are unsuitable as such for further reactions in the overall process according to the invention and must first be converted into the required monochlorination products by additional reactions. Other known chlorinating agents such as chlorine, hypochlorite, phosphorus trichloride and phosphorus oxychloride lead to non-uniform products and low yields. The reaction described above, on the other hand, proceeds surprisingly smoothly and what is even more surprising the that the reaction is not accompanied by any significant hydrolysis of the chlorinating agent which normally can only be used in an anhydrous medium.

The 4-halogen-pyrazolone-5-imines according to the invention (formula I, $R^2=H$) may also be obtained by monohalogenation of 5-aminopyrazoles (III) which are unsubstituted in the 4-position by N-chlorosuccinimide or N-bromosuccinimide in an aprotic solvent such as methylene chloride, dichlorobenzene or acetonitrile. These methods of halogenation also proceed very smoothly and result in high yields of the monohalogenation products.

The 4-halogen-pyrazolone-5-imines according to the invention (formula I, $R^2=H$) are valuable intermediate products which open up the possibility of an advantageous, new overall process for the preparation of known compounds (II) which are valuable magenta couplers, as already mentioned above. These intermediate products may be subjected to a sequence of several successive stages of synthesis by which B. the compounds of formula I in which $R^2=H$ are converted into the corresponding pyrazolone-5-hydrazones (formula I, $R^2=NH_2$) by diazotization and reduction, C. the pyrazolone-5-hydrazones are then acylated to the corresponding pyrazolone-5-N'-acylhydrazones (formula I, $R^2=NH\text{-}CO\text{-}R^3$) by reaction with suitable acid chlorides, and D. the pyrazolone-5-N'-acylhydrazones obtained in stage C are cyclised with phosphoryl chloride in known manner to form compounds of formula II Stage B of the process according to the invention concerns the conversion of 4-halogen-pyrazolone-5-imine into the corresponding hydrazone. If this reaction is carried out in aqueous solution, diazotisation with sodium nitrite results in a virtually quantitative yield of a yellow nitroso compound instead of the desired diazonium salt.

It has now surprisingly been found that the difficultly soluble diazonium salt is obtained in excellent yields by diazotisation with an alkyl nitrite such as amyl nitrite or methyl nitrite in anhydrous methanolic HCl.

The diazonium salt is also formed by diazotisation with sodium nitrite in concentrated hydrochloric acid.

Subsequent reduction, e.g. with $SnCl_2$ in concentrated hydrochloric acid, yields the desired hydrazone.

This invention therefore also covers a process for the preparation of compounds of formula I in which $R^2=NH_2$ by diazotisation and reduction of compounds of formula I in which $R^2=H$, characterised in that diazotisation is carried out with alkyl nitrite, preferably $C_1$-$C_5$-alkyl nitrite, in anhydrous methanolic HCl, or with an alkali metal nitrite, preferably $NaNO_2$, in concentrated hydrochloric acid.

Stage C of the process according to the invention concerns the acylation of 4-halogen-pyrazolone-5-hydrazone with suitable acid chlorides. These generally correspond to the formula $R^3\text{-}CO\text{-}Cl$ in which $R^3$ has the meaning already indicated. When carried out under the usual conditions of acylation, this reaction generally yields two isomeric diacyl compounds, even when the acylating agent is used in excess, and acylation occurs not only on the hydrazine group, as required, but also on one of the two ring nitrogen atoms and only small quantities of the desired monoacylation product are obtained. Acylation of 3-methyl-4-chloro-pyrazolone-5-hydrazone (formula I, $R^1=CH_3$, $R^2=NH_2$, $X=Cl$), for example, results in the formation of compounds corresponding to the following formulae

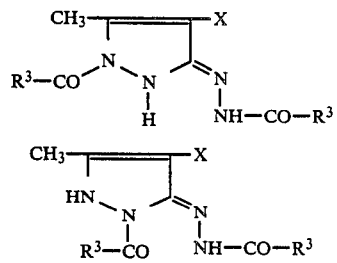

approximately in the ratio of 1:1.

It is surprisingly found that formation of the unwanted diacylation products can be to a large extent suppressed and the desired monoacylation product (formula I, $R^2=NH\text{-}CO\text{-}R^3$) obtained in high yields and a high degree of purity if the reaction is carried out in a diphasic medium of water and an organic solvent which is only slightly miscible with water and preferably has a specific gravity greater than 1, e.g. methylene chloride.

This invention therefore also covers a process for the preparation of compounds corresponding to formula I in which $R^2=NH\text{-}CO\text{-}R^3$ by the acylation of compounds of formula I in which $R^2=NH_2$ with an acylating agent of the formula $R^3\text{-}CO\text{-}Cl$ in which $R^3$ has one of the meanings indicated, characterised in that acylation is carried out in a diphasic medium of water and an organic solvent which is only slightly miscible with water, preferably methylene chloride. In this process, hydrazone, for example in the form of its hydrochloride, is introduced into the reaction vessel in the aqueous phase and the acylating agent dissolved in the organic solvent is added. The monoacylation product generally precipitates in crystalline form. The diphasic reaction medium evidently provides particularly advantageous conditions preventing further acylation of the monoacylation product. The reaction is suitably carried out at low temperatures, for example at $-5°$ C. to $15°$ C.

This reaction is normally followed in known manner by a ring closure reaction by which the bicyclic ring system, pyrazolo[3,2-c]-s-triazole is formed. This reaction is already known in principle, e.g. from DE-A-1 810 462. The products directly obtained from the ring closure reaction in the process according to the invention contain in their coupling position a group which can be released in the colour coupling reaction, namely a halogen atom X. This constitutes a considerable advantage of the overall process according to the invention, especially since the products directly obtained from the ring closure reaction in the known processes contain an alkoxycarbonyl group in this position of the pyrazolo[3,2-c]-s-triazole so that the coupling position is blocked. The products directly obtained from the ring closure reaction of the known processes therefore do not constitute couplers and must be subjected to further, very complicated processes, difficult to control on a technical scale and involving considerable losses, so that they may be converted step by step, by saponification, decarboxylation and halogenation, into compounds which by the process according to this invention are obtained directly from the aforesaid ring closure reaction.

The advantage and success of the overall process according to the invention are thus decisively provided by the fact that the required halogenation, i.e. the introduction of a halogen atom, in particular a chlorine atom, into that position of the organic intermediate product which is subsequently to form the coupling position of the pyrazolo[3,2-c]-s-triazole coupler, namely the 7-position, occurs at a comparatively early stage of the overall process according to the invention.

The products directly obtained from the ring closure reaction carried out in the course of subsequent stages of the process according to the invention, i.e. the ring closure reaction carried out with compounds of formula I in which $R^2=NH-CO-R^3$, have the characteristics of couplers, as already mentioned. This does not debar them from being further modified in known manner at functional groups such as COOH, OH, $NO_2$ or $NH_2$ present in the groups $R^1$ and $R^3$, and a wide variety of groups such as ballast groups, solubilizing groups, reactive groups and the like can be introduced into the coupler molecule in these positions so that a colour coupler with optimum properties can finally be obtained.

EXAMPLE 1

3-Methyl-4-chloro-pyrazolone-imine-(5) hydrochloride ($C_6H_4N_3Cl.HCl$)

600 g of 3-Methyl-pyrazolone-imine-(5) in 1 l of water were introduced into the reaction vessel and 1 l of concentrated hydrochloric acid was added. The temperature rose to 55° C. to 60° C. 600 ml of sulphuryl chloride were added dropwise at 65° C. to 70° C. over a period of about 3 hours. The gaseous HCl and $SO_2$ evolved were discharged through an absorption attachment. The clear, yellow solution obtained was cooled to 10° C., and the desired reaction product precipitated as a thick paste.

The product was isolated by suction filtration, washed three times with 350 ml of acetone and dried in air.

Yield: 682 g=65.5% of theoretical
Mp.: 215° to 217° C.

EXAMPLE 2

3-Methyl-4-chloro-pyrazolone-(5)-hydrazone hydrochloride ($C_4H_7ClN_4.HCl$)

168 g of 3-Methyl-4-chloro-pyrazolone-(5)-imine hydrochloride (product from Example 1) were suspended in 750 ml of concentrated hydrochloric acid and cooled to 0° C., and a solution of 73 g of $NaNO_2$ in 150 ml of water was added dropwise at this temperature. The imine slowly went into solution and a small quantity of sodium chloride precipitated. The reaction mixture was then stirred for 30 minutes and a solution of 500 g of hydrated tin(II) chloride in 750 ml of concentrated hydrochloric acid was added dropwise at 0° C. The time required for this addition of stannous chloride was about 3 hours. The desired hydrazone separated as a thick paste and was removed by suction filtration, washed three times with 300 ml of cold acetonitrile and dried in air.

Yield: 198 g=90% of theoretical,
Mp.: 165° to 170° C.

EXAMPLE 3

3-Methyl-4-chloro-pyrazolone-(5)-N'-ω-4-nitrophenyl-butyryl hydrazone ($C_{14}H_{18}N_5O_4Cl$)

146 g (75%) 3-Methyl-4-chloro-pyrazolone-(5)-hydrazone hydrochloride (product from Example 2) were dissolved in 1.1 l of water and cooled to 0° C., and 107 g of sodium acetate were added. 240 ml of methylene chloride were then added and 114 g of p-nitrophenylbutyric acid chloride dissolved in 240 ml of methylene chloride were added dropwise with very vigorous stirring at 0° C. The hydrazide precipitated in the process. Stirring was then continued for 15 minutes and the product obtained was separated by suction filtration and washed three times with 200 ml of methylene chloride. The product was stirred into 1 l of water, suction filtered and washed three times with 200 ml of water. The product was dried at 40° C.

Yield: 138 g=74% of theoretical
Mp.: 108° to 111° C.

EXAMPLE 4

7-Chloro-6-methyl-3-(p-nitrophenylbutyl)-1H-pyrazolo[3,2-c]-s-triazole ($C_{14}H_{14}N_5O_2Cl$)

160 g of 3-Methyl-4-chloro-pyrazolone-(5)-N'-ω-4-nitrophenyl-butyrylhydrazone (product from Example 3) were suspended or dissolved in 630 ml of Sulpholan and heated to 40° C. 128 ml of phosphorus oxychloride were run in at this temperature within 1 minute. A complex precipitated and the temperature rose to 80°–90° C. A clear solution formed when this temperature was reached. The solution was stirred for 15 minutes at 115° C. and then poured with rapid stirring into 2500 ml of water. The excess phosphorus oxychloride decomposed and the reaction product slowly crystalized. The product was separated by suction filtration after one hour and repeatedly washed with water.

The crude product obtained was suspended in 450 ml of ethanol and heated to 50° C. in a water bath, and 75 g of sodium acetate were added. The reaction mixture was then stirred for 5 minutes, poured into 1 l of water with stirring, suction filtered and washed with water and after the product had been sucked dry it was again stirred up with 300 ml of ethanol. It was then again suction filtered and washed with ethanol until the washings were colourless. The product was dried under vacuum at a maximum temperature of 100° C.

Yield: 100 g=73% of theoretical
Mp.: 182° C.

EXAMPLE 5

3-Methyl-4-chloro-pyrazolone-5-imine hydrochloride 450 g of 3-Methylpyrazolone-5-imine were dissolved in 3.6 l of methylene chloride. 612 g of N-chlorosuccinimide were then introduced at 10° C. The product precipitated and was separated by suction filtration and washed with methylene chloride.

Crude yield: 718 g

The crude product was dissolved in 1 l of hydrochloric acid, cooled (succinimide remained in solution), separated by suction filtration and washed with cold concentrated hydrochloric acid and then with acetonitrile.

Yield: 390 g
Mp.: >200° C.

EXAMPLE 6

3-Methyl-4-bromo-pyrazolone-5-imine hydrochloride 20 g of 3-Methylpyrazolone-5-imine were dissolved in 220 g of methylene chloride. 37 g of N-bromosuccinimide were then introduced at 20° C. The bromine compound precipitated together with succinimide and was suction filtered and washed with methylene chloride.

EXAMPLE 7

3-Methyl-4-chloropyrazolone-5-hydrazone hydrochloride 350 g of 3-Methyl-4-chloropyrazole-5-imine hydrochloride were dissolved in 1670 ml of methanol and 830 ml of methanolic hydrochloric acid. 270 g of amyl nitrite were added dropwise at 10° C. within 30 minutes. After one hour at 0° C., the reaction mixture was cooled to −10° C. and the precipitated diazonium salt was separated by suction filtration. The diazonium salt was dissolved in 1750 ml of concentrated hydrochloric acid which had been cooled to 0° C. and a solution of 1160 g of $SnCl_2.2H_2O$ in 1750 ml of concentrated hydrochloric acid was added dropwise at 0° to −5° C. The hydrazone precipitated and was separated by suction filtration and washed three times with 400 ml of acetonitrile.

Yield: 280 g.

We claim:

1. Compounds corresponding to formula I

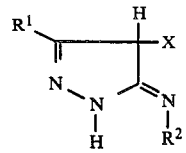

wherein

X denotes chlorine or bromine, $R^1$ denotes H, alkyl with 1 to 18 carbon atoms or a phenyl group which may be substituted with alkyl or alkoxy, $R^2$ denotes $NH_2$ or $NH-CO-R^3$, $R^3$ denotes alkyl with 1 to 18 carbon atoms, a benzyl, phenethyl or ω-phenylpropyl group wherein the phenyl group may be substituted by halogen, alkoxy, nitro or acylamino, a phenyl group which may be substituted by alkyl, alkoxy, chlorine or amino, or a thienyl group.

2. Compounds corresponding to formula I wherein

X denotes chlorine, $R^1$ denotes alkyl with 1 to 4 carbon atoms, $R^2$ denotes $NH_2$ or $NH-CO-R^3$ and $R^3$ denotes alkyl or a benzyl, phenethyl or ω-phenylpropyl group wherein the phenyl group may be substituted by halogen, alkoxy, nitro, or acylamino.

* * * * *